(12) United States Patent
Schraga

(10) Patent No.: US 6,228,100 B1
(45) Date of Patent: May 8, 2001

(54) MULTI-USE LANCET DEVICE

(76) Inventor: Steven Schraga, 9433 Byron Ave., Surfside, FL (US) 33154

( * ) Notice: Subject to any disclaimer, the term of this patent is extended or adjusted under 35 U.S.C. 154(b) by 0 days.

(21) Appl. No.: 09/425,942

(22) Filed: Oct. 25, 1999

(51) Int. Cl.[7] ................................................ A61B 17/32
(52) U.S. Cl. ........................................................ 606/183
(58) Field of Search .................................. 606/181–183, 606/161, 167, 168, 185, 188, 184; 604/136, 137, 157, 46; 600/556, 557

(56) References Cited

U.S. PATENT DOCUMENTS 4,794,926 * 1/1989 Munsch et al. .................. 606/183 X
4,823,806 * 4/1989 Bajada ................................. 600/557
5,514,152 * 5/1996 Smith ................................... 606/181

* cited by examiner

Primary Examiner—Michael H. Thaler
Assistant Examiner—(Vikki) Hoa B. Trinh
(74) Attorney, Agent, or Firm—Malloy & Malloy, P.A.

(57) ABSTRACT

A multi-use lancet device having a lancet receiving assembly containing at least two lancets disposed therein and structured to be independently moveable between a cocked and a fired orientation, and a firing assembly movably and operatively coupled with the lancet receiving assembly so as to be selectively and independently positioned in operative engagement with each of the lancets in order to define an active one of the lancets. The firing assembly is also structured to selectively move at least the active lancet between its cocked and its fired orientations.

39 Claims, 2 Drawing Sheets

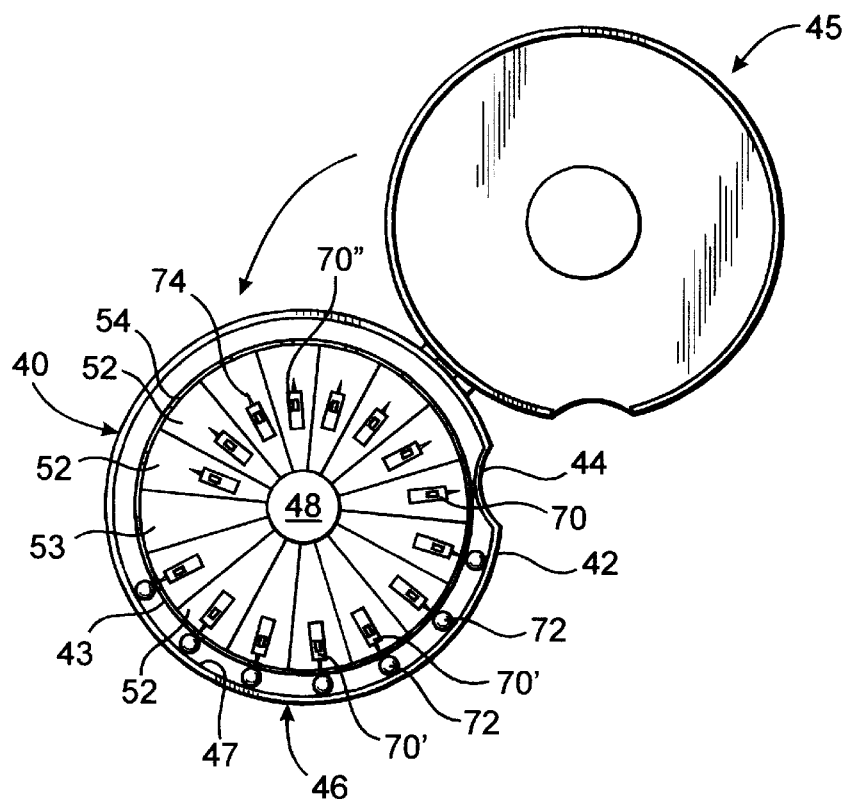
FIG. 4
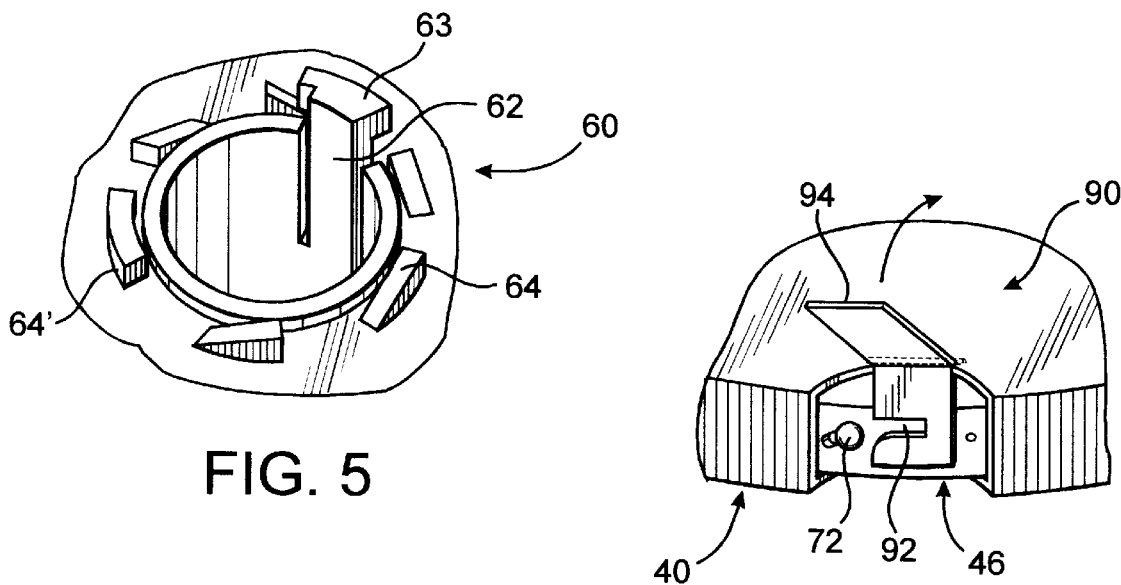
FIG. 5
FIG. 6

MULTI-USE LANCET DEVICE

BACKGROUND OF THE INVENTION

1. Field of the Invention

The present invention relates to a multi-use lancet device structured to safely and effectively allow a user to employ a single device, repeated times, each time providing and preserving the sterility required, but in a manner which does not require the user to manipulate and remove a used lancet and reload a new lancet into the device each time a new use is required. The device as such provides for only a single use of each individual lancet, while providing a plurality of sterile lancets for safe and effective use by a patient or medical practitioner.

2. Description of the Related Art

Lancet devices are commonly utilized devices which allow patients and medical practitioners to "prick" a patient's skin in order to effectively obtain a blood sample for a variety of tests. Typically these lancet devices involve the driving of a lancet tip into the patient's skin so as to result in bleeding by the patient, thereby allowing the sample to be gathered. Moreover, although these tests are often performed in a hospital or laboratory environment, because of the prevalence of many home testing kits, more and more individual patients are turning to self testing, and as a result, independently utilize the lancet device so as to obtain their own blood sample.

Conventional lancet devices available in the art typically range from single use, disposable lancets, to re-useable lancet devices wherein an individual lancet can be removed and replaced after each use. As to the disposable lancets, they are generally effective to ensure that individual users do not reuse a previously contaminated lancet, and provide a certain cost effective degree of effective use. Naturally, however, when a patient or practitioner must repeatedly take blood samples, it can become quite costly and indeed quite cumbersome to have a large number of the individual disposable devices available. To this end, reusable lancet devices are becoming increasingly popular.

In the reusable lancet devices, small lancets having protruding piercing tips are typically provided in bulk for removal and replacement into the lancet device itself. For example, most lancet devices include a housing which is opened so as to allow the user to remove a contaminated and/or used lancet. During such removal, the user must take great care to ensure that he/she does not inadvertently prick themselves with the contaminated lancet tip, and indeed, there are a variety of inventions in the field of art relating to the reusable lancet devices which specifically address the concerns associated with the safe removal and disposal of used lancets. Once the used lancet has been removed and paced in an appropriate sharps box, however, a new, sterile lancet must necessarily be introduced into the device, also in a safe fashion, and the device reassembled and cocked for the subsequent use. While such reusable lancet devices provide users with certain economic benefits, there is still a concern that removal and replacement of the individual lancets within the reusable lancet device is a generally hazardous practice that could often lead to inadvertent lacerations and contamination. Furthermore, the general inconvenience of having a large plurality of loose lancets available for repeated reloading can often be cumbersome and/or inconvenient, with the new sterile lancets not always being maintained with the reusable lancet device itself.

As a result, it would be beneficial to provide a lancet device which not only can be effectively utilized so as to prick a patient's skin and achieve blood sampling, but which also further increases the safe and efficient use of the device by eliminating the need for a user to remove each used lancet prior to reusing the device. Furthermore, such a device should preferably still maintain a substantial degree of safety by ensuring that a used lancet tip cannot inadvertently be reused, but should also provide a substantially great degree of convenience, allowing repeated and continuous use of the device to be achieved in an effective manner. Moreover, such a device should be effectively configured to allow facilitated reuse, however, only after a number of safe, sterile uses have already been achieved.

SUMMARY OF THE INVENTION

The present invention relates to a multi-use lancet device. In particular, the multi-use lancet device includes a lancet receiving assembly and a firing assembly operatively associated with one another. At least partially disposed in the lancet receiving assembly are at least two, but preferably a plurality of lancets. The lancets are preferably of the type including a body and a protruding piercing tip which actually pricks the patient during use. Moreover, each of the lancets is also structured to be independently movable between a cocked and fired orientation within the lancet receiving assembly.

The firing assembly of the present invention is preferably movably coupled in association with the lancet receiving assembly. As a result, the firing assembly is preferably selectively and independently positionable into operative engagement with each of the lancets, in doing so defining an active one of the lancets. Preferably, this operative engagement with each of the lancets is achieved in a substantially sequential fashion, such that after each use of an active lancet, the firing assembly can be moved to another, unused lancet so as to define it as the active lancet. The firing assembly is also structured to selectively move at least the active lancet between its cocked and its fired orientations. In particular, the lancet is preferably first positioned into the cocked orientation, and the firing assembly is structured to preferably to drive or move the lancet through a piercing orientation, wherein the patient's skin is pierced, and then to its fired orientation, which preferably conceals the pointed piercing tip to prevent inadvertent contact by a user.

In addition to being movably disposed with the firing assembly, the lancet receiving assembly is also preferably at least partially removably coupled to the firing assembly. As a result, once each of the lancets have been utilized and moved to their fired orientations, the at least partial removal of the lancet receiving assembly allows access and efficient removal of the used lancets so as to provide for effective replacement with new, sterile lancets. Accordingly, reloading of the multi-use lancet device of the present invention generally must only take place one time between a large series of separate uses.

BRIEF DESCRIPTION OF THE DRAWINGS

For a fuller understanding of the nature of the present invention, reference should be had to the following detailed description taken in connection with the accompanying drawings in which:

FIG. 4 is a bottom view of the multi-use lancet device of the present invention including a lid assembly to allow access to the guide regions of the lancet receiving assembly;

FIG. 5 is an isolated perspective view of an embodiment of the ratcheting assembly of the present invention which permits relative movement between the firing assembly and at least a portion of the lancet receiving assembly; and FIG. 6 is an isolated view of the tip guard removal assembly of the present invention.

Like reference numerals refer to like parts throughout the several views of the drawings.

DETAILED DESCRIPTION OF THE PREFERRED EMBODIMENT

Figure 1:
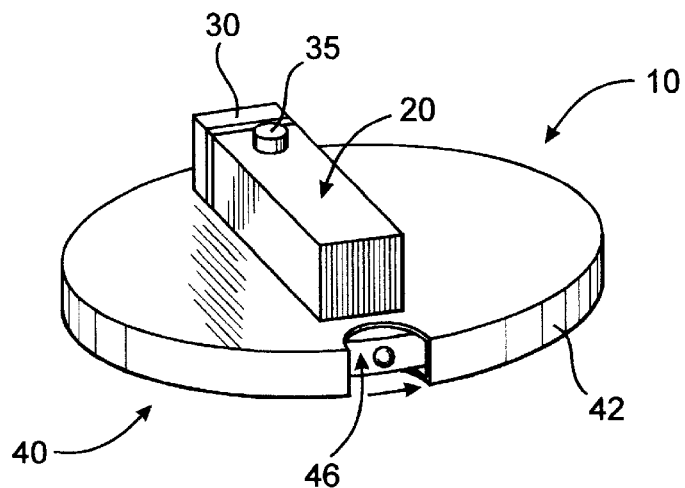
FIG. 1 is a perspective view of the preferred multi-use lancet device of the present invention.

As shown throughout the Figures, the present invention is directed towards a multi-use lancet device, generally indicated as 10. In particular, the multi-use lancet device 10 is structured to contain at least two, but preferably a plurality of individual lancets 70, each of which includes a pointed piercing tip 74 for safe and effective use. Moreover, the lancet device 10 of the present invention is preferably structured to provide for the safe and sequential firing of each of the lancets, only a single time, thereby eliminating the requirement that a user remove and replace each lancet individually before and after each use.

With reference particularly to the drawings, the lancet device 10 of the present invention includes a lancet receiving assembly, generally 40, operatively associated with a firing assembly, generally 20. Looking first to the lancet receiving assembly 40, it is structured to contain at least two but preferably a plurality of lancets 70 therein in an operative useable orientation. Along these lines, the lancet receiving assembly 40 preferably includes a primary housing 46 with a series of guide regions 52 defined therein. Each of the guide regions 52 is structured to movably contain at least one of the individual lancets 70 therein. Additionally, the primary housing 46 of lancet receiving assembly 40 preferably includes a plurality of piercing openings 54. In particular, one of the piercing openings 54 is preferably disposed in operative association with each of the guide regions 52, and may be rather small so as to merely accommodate the pointed tip 74 of a lancet 70 being fired and/or may be larger allowing a front end of the body along with the pointed tip 74 to effectively protrude from the primary housing 46 of the lancet receiving assembly 40 through an exposed or active one of the piercing opening.

Also as illustrated in the Figures, the lancet receiving assembly 40 is structured to receive an active lancet 70, which is the lancet that is in position to be utilized and fired at a given point in time, as well as one or more used lancets 70" which have already been fired, and/or one or more un-used lancets 70' which are sterile and include a removable tip guard 72 protectively disposed over the piercing tip 74 of the un-used lancet 70'. In particular, it is noted, and as will be described in greater detail subsequently, that initially all of the lancets are un-used, protected lancets 70' having a tip guard 72. Only after a first lancet is moved into an operative firing position and thereby becomes the active lancet 70 is the tip guard 72 to be removed. Specifically, it is noted that the tip guard 72 preferably protrudes from the primary housing 46 of the lancet receiving assembly 40 such that when the individual lancet moves into position to be the active lancet 70, the tip guard 72 may be effectively grasped or otherwise removed so as to allow the exposed piercing tip 74 of the lancet 70 to effectively pierce the skin during normal operation of the multi-use lancet device 10, as will be described. For example, and as illustrated in FIG. 6, a tip guard removal assembly 90 may be provided, the tip guard removal assembly 90 including a channel 92 defined therein wherein the tip guard 72 moves upon the lancet receiving assembly being at least partially rotated to activate a new, un-used lancet, as will be described. Once the tip guard moves into the channel 92, the tip guard removal assembly 90 can be pivoted, such as by pressing an actuation end 94 thereof, and thereby causing the tip guard 72 to be removed form the lancet 70. Preferably the tip guard removal assembly 90 is generally biased so as to be prepared to receive a subsequent tip guard 72 upon activation of a subsequent lancet.

It is also noted that the tip guard 72, when secured to the lancet, preferably limits the movement of the lancet within the guide regions 52 and thereby maintains the lancet properly positioned for engagement by the downwardly depending segment 25 of the engagement assembly 24, as will be described. Moreover, after each lancet has been utilized, it thereafter becomes a fired or used lancet 70" which is preferably safely contained within the guide region 54, and/or an interior shield 47 until disposal thereof is effectively desired.

Looking to FIGS. 1 and 4, the present invention also preferably includes a shielding assembly, generally 42. The shielding assembly 42 is preferably structured to generally surround and protect the remainder of the lancet receiving assembly 40 including the primary housing 46. Along these lines, it is noted that the shielding assembly 42 preferably comprises a part of the lancet receiving assembly 40 and may be separable and/or integrally formed with the firing assembly. In either instance, the shielding assembly 42 is structured to be operatively disposed in at least partially shielding orientation to the primary housing 46 of the lancet receiving assembly 40 when it is in an operative position within the multi-use lancet device 10 of the present invention.

Looking in further detail to the shielding assembly 42, it preferably includes a piercing zone as at 44, which is configured to expose at least one of the piercing openings of one of the guide regions 52. The piercing zone 44 preferably includes a generally curved and/or rounded configuration structured to correspond the contour of a patient's finger where the piercing will generally take place. Moreover, the piercing zone 44 is also configured so as to allow the body part being pierced to be positioned in closer proximity to the exposed piercing opening 54 when the piercing tip 74 of the active lancet 70 passes even only a slight distance therethrough. As best seen in FIG. 4, this spacing and/or gap that is defined by the piercing zone 44 in the shielding assembly 42 can be contrasted with the preferred spacing that remains between the remainder of the shielding assembly 42 and the periphery of the guide regions of the lancet receiving assembly 40. In particular, this additional spacing is preferred such that the removable tip guards 72 of the un-used lancets 70' can also be maintained within the shielding assembly 42, and only when the lancet moves to the piercing zone 44 so as to become the active lancet 70 can the removable shielding tip 72 be accessed for removal.

Figure 2:
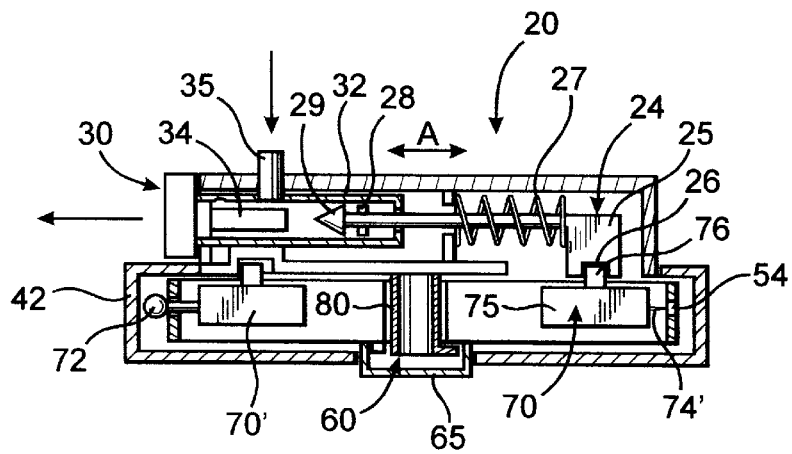
FIG. 2 is a cross-section view of an embodiment of the multi-use lancet device of the present invention.
Figure 3:
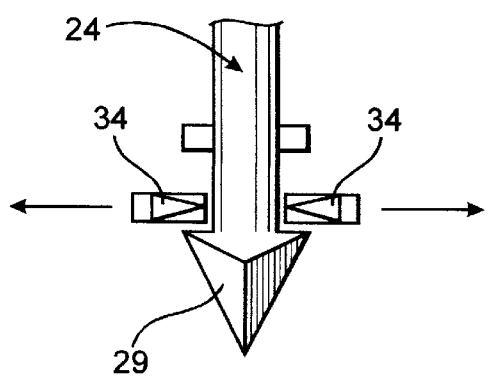
FIG. 3 is an isolated top view of a portion of an embodiment of the actuation assembly of the present invention which releases the engagement element from its cocked orientation.

In a first embodiment of the present invention, as illustrated in FIG. 2, the shielding assembly 42 is preferably formed as part of and/or in association with the primary housing 46 of the lancet receiving assembly 40 so as to be completely removable from the firing assembly 20, to be described in greater detail subsequently. As a result, once all of the lancets contained within the lancet receiving assembly 40 have been utilized, the entire lancet receiving assembly 40, including the primary housing 46 and shielding assembly 42 can be effectively removed from the firing assembly 20 and replaced with a full, unused lancet receiving assembly 40, in a cartridge type form. Alternatively, however, as in the embodiment of FIG. 4, a lid assembly 45 may be hingedly and/or otherwise removably secured to the shielding assembly 42 and/or directly to the primary portion of the lancet receiving assembly 40 so as to selectively expose the primary housing 46 and/or guide regions 52 of the lancet receiving assembly 40. In such an embodiment, the primary housing 46 can be completely removed from the shielding assembly 42, and/or the individual guide regions 52 can be exposed so as to allow the used lancets 70" to merely be removed therefrom, such as by turning over the device into a disposal area, followed by facilitated reloading of shielded, un-used lancets 70' into each of the appropriate guide regions 52. In this second embodiment wherein a lid assembly 45 is provided and the primary housing 46 may be removed, the lancets 70 may be configured, such as with a biasing element, to remain within the primary housing 46 after they have been fired, or as illustrated, an interior shield 47 may be provided in association with the primary housing 46 for unitary removal therewith, thereby ensuring concealment of the used lancets 70" and avoiding the need for a special sharps box.

Turning to FIGS. 1 and 2, and looking in particular to the firing assembly 20 of the present invention, it preferably includes a housing 22 wherein preferably a substantial portion of the internal mechanism of the firing assembly 20 is contained. In particular, as illustrated in FIG. 2, the firing assembly includes an engagement element 24 movably disposed therein and structured to operatively engage and indeed define, at least the active lancet 70. Specifically, the engagement element 24 is structured to move from a cocked orientation through a piercing orientation, and ultimately to a fired orientation. In doing so, the engagement element 24 operatively engages the active lancet 70 also moving it therewith from its cocked orientation through its piercing orientation, wherein the piercing tip 74 passes through the exposed piercing opening 54 of a corresponding guide region 52, and finally into its fired orientation wherein the piercing tip 74 is generally concealed within the guide region 52.

In order to facilitate the operative engagement between the engagement element 24 and the active lancet 70, the engagement element 24 preferably includes a downwardly depending segment 25 having a trough or gap 26 defined therein. This downwardly depending segment is structured to operatively engage a corresponding upwardly depending segment 76 which is formed on preferably each of the lancets. As a result, when lateral movement, as illustrated by arrow A in FIG. 2 is achieved, the downwardly depending segment 25 catches the upwardly depending segment 76 of the lancet providing for effective lateral or radial movement thereof. When, however, the lancet receiving assembly 40 and the firing assembly 20 at least partially move and/or rotate relative to one another, however, the sides of the downwardly depending segment 25 are preferably open so as to allow the downwardly depending segment 25 to freely pass from the upwardly depending segment 76 of the active lancet 70. Additionally, when the lancet receiving assembly 40 at least partially rotates relative to the firing assembly 20, a new unused lancet 70' moves into operative engagement, with its upwardly depending segment 76 being engaged by the downwardly depending segment 25 of the engagement assembly 20. At that point, the protective tip 72 can be removed and the firing assembly cocked, as will be described. Also, it is noted that although the illustrated lancet receiving assembly includes generally co-planer guide regions 52 and is structured to rotate relative to the firing assembly 20, a straight line or vertically rotating configuration could also be achieved so as to sequentially position unused lancets into operative engagement with the firing assembly 20 and prevent re-use of used lancets. Also, the entire lancet receiving assembly 40 may be structured to rotate, and/or only a portion thereof, such as the primary housing 46 by providing exterior access thereto at a hub or handle 48.

Although many firing structures used in various single use lancets could be employed, the engagement assembly 24 of the illustrated embodiment of the present invention is preferably structured to be fired as a result of a biasing element 27, such as a coil spring. The biasing element 27 is structured to be generally compressed when the engagement assembly 24 and accordingly the active lancet 70 are retracted into the cocked orientation, such that when it is released the engagement element is driven through the piercing orientation and into the fired orientation.

In order to achieve effective cocking of the engagement assembly 24 once it is operatively engaged with an unused, active lancet 70, a cocking assembly, generally 30 is provided. In particular, the cocking assembly 30 preferably includes at least one or a pair of inwardly dependingly fingers 32 which operatively engage the engagement assembly 24, as at flanges 28. By pulling out the cocking assembly 30, the engagement assembly 24 is effectively pulled into its cocked orientation. Once in the cocked orientation, an enlarged head 29 associated with the engagement assembly 24 is preferably captured or retained by one or more retention elements 34 which comprise part of an actuation assembly of the present invention. Specifically, the retention elements 34 preferably tend to bias inwardly so as to captivate the enlarged head 29 of the engagement assembly 24 when it is pulled into the cocked orientation by the cocking assembly 30. Along these lines, the enlarged head 29 preferably includes a generally pointed and/or tapered configuration which matches a corresponding pointed and/or tapered configuration on a confronting face of the retention elements 34, such that when the engagement assembly 24 is pulled into the cocked orientation, the pointed configuration of the enlarged head 29 tends to separate the retention elements 34. A back side of the enlarged head 29, however, preferably includes a more flattened configuration such that affirmative separation of the retention elements 34 is required in order to release the engagement assembly 24 and allow passage of the enlarged head 29 therethrough to result in firing of the engagement assembly 24, and accordingly, the active lancet 70. Along these lines, the actuation assembly preferably includes an actuation button 35 which may be spring biased and/or exposed in a rear or top of the housing 29, as illustrated in FIG. 2. The actuation button 35 preferably includes a contoured configuration which is structured to engage the retention elements 34 and results in a spreading and/or spacing of the retention elements 34 to permit release of the enlarged head 29 and firing of the engagement assembly 24. The retention elements 34, in the embodiment wherein the actuation button 35 is disposed in a top of the housing also preferably include generally slopped upper surfaces, such that a matching pointed configuration of the actuation button 35 tends to gradually and effectively urge the retention elements 34 into a sufficient spaced apart relation from one another so as to allow release and firing of the engagement assembly 20. Also, if desired, a mechanism whereby cocking and rotation of the lancet receiving assembly 40 are simultaneously achieved could also be provided.

From the preceding it is seen that once the active lancet 70 has been fired, the biasing element 27 that urges the engagement assembly 24 will push the piercing tip 74 of the active lancet through the exposed piercing opening 54. The normal tendencies of the biasing element 27, however, will tend to generally pull the engagement assembly 24 and the active lancet 70 back out of its fully extended piercing orientation and into a preferably generally concealed, at rest, fired orientation. At that point, once the active lancet 70 has been utilized, relative movement between the firing assembly 20 and the lancet receiving assembly 40 is preferably achieved so as to effectively move a next of the unused lancets 70' into operative engagement with the engagement assembly 24 so as to define it as the active lancet 70. In order to achieve this relative movement between the firing assembly 20 and the lancet receiving assembly 40. A mount hub 80 is preferably provided and extends from the firing assembly 20 through the lancet receiving assembly 40, generally providing an axis of rotation for the lancet receiving assembly 40. Additionally, it is also preferred that a ratchet configuration 60, as illustrated in FIG. 5, be effectuated between the lancet receiving assembly 40 and the hub 80 coupled to the firing assembly 20. In particular, as illustrated in FIG. 5, the hub 80 preferably includes one or more fingers 62, each of which includes a ratchet head 63. The finger 62 may also be configured to be generally biasable inward, when desired, so as to allow for effective removal of the lancet receiving assembly 40 from the hub 80. Significantly, however, the ratchet head 63 is preferably provided with a generally slopped configuration at one edge thereof and a generally flat configuration at an opposite edge thereof. The ratchet head 63 is structured to slide over a plurality of ratchet elements 64 disposed preferably on the lancet receiving assembly 40 about the periphery of the hub 80. The ratchet elements 64 also preferably include a mating slopped configuration on one side thereof and a generally flat configuration on an opposite side thereof so as to permit relative movement between the ratchet head 63 and the ratchet element 64 only in a singled direction. For example, the mating slopped configurations allow the ratchet head 63 to slide thereover and be partially displaced, however, when the ratchet head 63 moves beyond the ratchet element 64, the generally flat confronting surfaces abut one another preventing rotation and/or relative movement between the lancet receiving assembly 40 and the firing assembly 20 in the opposite direction. Moreover, preferably one stopper element 64' is provided once a complete revolution has been achieved and all of the lancets have been used a single time. The stopper element 64' preferably includes a flattened configuration on both sides thereof so as to generally resist and/or prevent movement of the ratchet head 63 thereover, and to thereby block further rotation and/or relative movement between the lancet receiving assembly 40 and the firing assembly 20. Likewise, the lancet receiving assembly 40 preferably includes a safety region 53 defined therein. In particular, when the restrictor assembly 64' is reached, the safety region 53 is preferably disposed at the piercing zone 44 of the shielding assembly 42, thereby preventing a used lancet from remaining in the firing zone 44 and potentially being reused. Likewise, the ratchet assembly may also be configured such that the safety region 53 is disposed in the active position when a new "cartridge" of un-used lancets is secured within the lancet device.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,
What is claimed is:

1. A multi-use lancet device comprising:
   (a) a lancet receiving assembly;
   (b) at least two lancets at least partially disposed in said lancet receiving assembly and structured to be independently moveable between a cocked and a fired orientation; and
   (c) a firing assembly structured to selectively and independently engage at least a plurality of said lancets so as to selectively move at least an active one of said lancets between said cocked and said fired orientations wherein said firing assembly is laterally offset from the active one of said lancets.

2. A multi-use lancet device as recited in claim 1 wherein said firing assembly and said lancet receiving assembly are at least partially movably coupled with one another so as to define and engage said active lancet.

3. A multi-use lancet device as recited in claim 2 wherein said firing assembly is structured to be positioned in activating, engaging communication with each of said lancets only a single time.

4. A multi-use lancet device as recited in claim 3 wherein said firing assembly includes a mount hub at which said lancet receiving assembly is at least partially secured.

5. A multi-use lancet device as recited in claim 4 further including a restriction assembly structured to prevent said firing assembly from being re-positioned into said activating, engaging communication with a used one of said lancets which had previously been said active lancet.

6. A multi-use lancet device as recited in claim 4 wherein said lancet receiving assembly is removably secured to said firing assembly at said mount hub.

7. A multi-use lancet device as recited in claim 3 wherein said lancet receiving assembly includes a safety region associated with said firing assembly after said firing assembly has been positioned in said activating, engaging communication with all of said lancets.

8. A multi-use lancet device as recited in claim 1 wherein said firing assembly is structured to engage, so as to achieve movement between said cocked and said fired orientation, only one of said lancets at a time.

9. A multi-use lancet device as recited in claim 1 wherein said lancet receiving assembly includes at least one piercing opening structured and disposed to receive a tip of said active lancet therethrough upon movement of said active lancet between said cocked and fired orientations.

10. A multi-use lancet device as recited in claim 9 wherein said lancet receiving assembly includes only one exposed piercing opening wherethrough said tip of said active lancet may protrude, at a time.

11. A multi-use lancet device as recited in claim 1 wherein said lancets are removably disposed in said lancet receiving assembly.

12. A multi-use lancet device as recited in claim 11 wherein said lancet receiving assembly includes a primary housing having at least two guide regions defined therein wherein each of said lancets is movably disposed.

13. A multi-use lancet device as recited in claim 12 further comprising an access opening, said access opening structured to permit selective access to said primary housing so as to provide for the removal and introduction of said lancets into said lancet receiving assembly.

14. A multi-use lancet device as recited in claim 13 further comprising a lid assembly structured to selectively close said access openings.

15. A multi-use lancet device as recited in claim 13 wherein said lancet receiving assembly is at least partially removably coupled to said firing assembly so as to permit access to said access openings.

16. A multi-use lancet device as recited in claim 1 wherein said lancet receiving assembly includes at least two guide regions wherein each of said lancets is movably disposed.

17. A multi-use lancet device as recited in claim 16 wherein each of said guide regions is operatively associated with a piercing opening wherethrough a tip of said lancet protrudes upon movement between said cocked and said fired orientations.

18. A multi-use lancet device as recited in claim 17 further comprising a shielding assembly structured to expose at least one of said piercing openings at a time.

19. A multi-use lancet device as recited in claim 18 wherein said shielding assembly exposes only said piercing opening of said active lancet at a time.

20. A multi-use lancet device as recited in claim 16 wherein each of said lancets includes a removable tip guard structured to cover said tip of said lancet until use.

21. A multi-use lancet device as recited in claim 20 wherein said tip guard includes an enlarged configuration structured to be maintained exterior of a corresponding one of said guide regions at said piercing opening.

22. A multi-use lancet device as recited in claim 20 further comprising a shielding assembly structured to expose only one of said tip guards at a time.

23. A multi-use lancet device as recited in claim 1 wherein said lancet receiving assembly is removably coupled to said firing assembly.

24. A multi-use lancet device as recited in claim 1 wherein said firing assembly includes an engagement element structured to operatively engage said active lancet so as to result in movement of said active lancet between said cocked and said fired orientations.

25. A multi-use lancet device as recited in claim 24 wherein said engagement element is movably disposed between a cocked and a fired orientation so as to correspondingly move said active lancet between said cocked and said fired orientations thereof.

26. A multi-use lancet device as recited in claim 25 wherein said fired orientation of said engagement element and accordingly said active lancet position a tip of said active lancet in a concealed, non-piercing position.

27. A multi-use lancet device as recited in claim 25 wherein said firing assembly and said engagement element are movably disposed relative to at least a portion of said lancet receiving assembly such that said engagement element is selectively moveable into operative engagement with at least an unused one of said lancets so as to define said active lancet.

28. A multi-use lancet device as recited in claim 25 wherein each of said lancets includes an upwardly depending segment structured to be operatively engaged by said engagement element.

29. A multi-use lancet device as recited in claim 28 wherein said engagement element includes a downwardly depending segment structured to operatively engage said upwardly depending segment of said active lancet at least during generally radial movement of said engagement element between said cocked and said fired orientations.

30. A multi-use lancet device as recited in claim 29 wherein said downwardly depending element of said engagement element is structured to move out of operative engagement with said upwardly depending segment of said active lancet upon said engagement element moving generally laterally into operative engagement with an adjacent one of said lancets.

31. A multi-use lancet device as recited in claim 25 further comprising a cocking assembly structured to at least temporarily maintain said engagement element and accordingly said active lancet in said cocked orientation.

32. A multi-use lancet device as recited in claim 31 further comprising an actuation assembly structured to move said engagement element and accordingly said active lancet from said cocked orientation.

33. A multi-use lancet device as recited in claim 32 wherein said engagement element is structured to at least temporarily move into a piercing orientation, wherein said tip of said active lancet is at least temporarily disposed in a corresponding exposed, piercing orientation, upon its being moved from said cocked orientation by said actuation assembly.

34. A multi-use lancet device as recited in claim 33 further comprising a biasing assembly structured to at least temporarily move said engagement element into said piercing orientation.

35. A multi-use lancet device as recited in claim 34 wherein said biasing assembly is further structured to move said engagement element into said fired orientation subsequent to said engagement element at least temporarily moving to said piercing orientation.

36. A multi-use lancet device as recited in claim 31 wherein said firing assembly comprises a housing, said housing structured to at least partially contain said engagement element in operative communication with said active lancet in said lancet receiving assembly.

37. A multi-use lancet device as recited in claim 36 wherein said cocking assembly comprises a retraction element structured to retract said engagement element from said fired orientation into said cocked orientation.

38. A multi-use lancet device comprising:
(a) a lancet receiving assembly;
(b) at least two lancets at least partially disposed in said lancet receiving assembly and structured to be independently moveable between a cocked and a fired orientation;
(c) a firing assembly, said firing assembly and said lancet receiving assembly at least partially movably coupled with one another;
(d) said firing assembly being selectively and independently positioned at least partially in operative engagement with at least a plurality of said lancets so as to define an active one of said lancets; and
(e) said firing assembly structured to selectively move at least said active lancet between said cocked and said fired orientations wherein said firing assembly is laterally offset from the active one of said lancets.

39. A multi-use lancet device comprising:
(a) a lancet receiving assembly;
(b) at least two lancets at least partially disposed in said lancet receiving assembly and structured to be independently moveable between a cocked and a fired orientation;
(c) a firing assembly structured to selectively and independently engage each of said lancets so as to selectively move at least an active one of said lancets between said cocked and said fired orientations;
(d) said firing assembly further including a mount hub at which said lancet receiving assembly is at least partially secured wherein said firing assembly is laterally offset from the active one of said lancets; and
(e) said mount hub including a ratchet configuration structured to permit said lancet receiving assembly to move in a single direction relative thereto in order to position said firing assembly in said activating, engaging communication with said lancets.

* * * * *